United States Patent
Bachur, Jr. et al.

(10) Patent No.: US 7,444,005 B2
(45) Date of Patent: Oct. 28, 2008

(54) APPARATUS AND METHOD FOR USING OPTICAL MOUSE ENGINE TO DETERMINE SPEED, DIRECTION, POSITION OF SCANNED DEVICE AND TO OBTAIN QUANTITATIVE OR QUALITATIVE DATA FROM SAME

(75) Inventors: Nicholas R. Bachur, Jr., Monkton, MD (US); Robert E. Armstrong, Hunt Valley, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 730 days.

(21) Appl. No.: 10/699,835

(22) Filed: Nov. 4, 2003

(65) Prior Publication Data

US 2005/0095697 A1    May 5, 2005

(51) Int. Cl.
*G06K 9/00* (2006.01)
*G01N 33/543* (2006.01)

(52) U.S. Cl. ............... 382/107; 435/287.2; 435/7.94; 435/4; 435/518; 356/39; 356/40; 356/41; 356/42; 235/462.13; 382/128; 382/321

(58) Field of Classification Search ............... 382/128, 382/107, 321; 436/169; 345/166; 435/287.2, 435/7.94, 4, 518; 235/462.13; 356/39, 40, 356/41, 42
See application file for complete search history.

(56) References Cited

U.S. PATENT DOCUMENTS

| | | | |
|---|---|---|---|
| 4,833,088 A * | 5/1989 | DeSimone et al. ............ 422/55 |
| 5,107,103 A | 4/1992 | Gruss et al. ............ 250/208.3 |
| 5,408,535 A * | 4/1995 | Howard et al. ............ 382/128 |
| 5,446,481 A | 8/1995 | Gillick et al. ............ 345/163 |
| 5,463,387 A | 10/1995 | Kato ............ 341/31 |
| 5,598,197 A | 1/1997 | Zaba ............ 347/75 |
| 5,619,231 A | 4/1997 | Shouen ............ 345/163 |
| 5,729,361 A * | 3/1998 | Suggs et al. ............ 358/505 |
| 5,793,357 A | 8/1998 | Ivey et al. ............ 345/166 |
| 5,994,710 A | 11/1999 | Knee et al. ............ 250/557 |
| 6,078,312 A | 6/2000 | Liebenow ............ 345/166 |
| 6,081,255 A | 6/2000 | Narabu ............ 345/158 |

(Continued)

OTHER PUBLICATIONS

"Agilent ADNS-2051 Optical Mouse Sensor Data Sheet" *Agilent Technologies*, pp. 1-40 (Jan. 9, 2002).

*Primary Examiner*—Andrew W. Johns
*Assistant Examiner*—Nancy Bitar
(74) *Attorney, Agent, or Firm*—Roylance, Abrams Bedno & Goodman, LLP

(57) ABSTRACT

A test strip reader is provided with an optical mouse integrated circuit sensor that reads the test line, reference line and control line of a lateral flow assay strip by light absorption and determines the position of the test strip beneath the image on the integrated circuit board using digital signal processing algorithms. The digital signal processing algorithms process the imaged surface at a very high rate (e.g., 1500 frames per second) to determine the direction and speed of movement of the lateral strip with respect to the reader optics and image capture components. The sensor outputs this position information in a quadrature pattern format. A microcontroller uses the known position of the strip with respect to the reader to calculate the optical absorption of each colored reagent line, and the diagnostic significance (i.e., either qualitative or quantitative) of the test strip.

13 Claims, 8 Drawing Sheets

U.S. PATENT DOCUMENTS

| | | | |
|---|---|---|---|
| 6,222,174 B1 | 4/2001 | Tullis et al. | 250/208.1 |
| 6,256,016 B1* | 7/2001 | Piot et al. | 345/166 |
| 6,281,882 B1* | 8/2001 | Gordon et al. | 345/166 |
| 6,392,632 B1* | 5/2002 | Lee | 345/158 |
| 6,394,952 B1 | 5/2002 | Anderson et al. | 600/300 |
| 6,452,683 B1 | 9/2002 | Kinrot et al. | 356/499 |
| 6,513,717 B2 | 2/2003 | Hannigan | 235/462.45 |
| 6,541,762 B2 | 4/2003 | Kang et al. | 250/239 |
| 6,762,751 B2* | 7/2004 | Kuan | 345/166 |
| 6,765,555 B2* | 7/2004 | Wu | 345/166 |
| 6,880,968 B1* | 4/2005 | Haar | 374/131 |
| 6,936,476 B1* | 8/2005 | Anderson et al. | 436/518 |
| 7,077,319 B2* | 7/2006 | Schnee et al. | 235/462.1 |
| 7,309,611 B2* | 12/2007 | DiNello et al. | 436/514 |
| 7,344,081 B2* | 3/2008 | Tseng | 235/462.13 |
| 2003/0085877 A1 | 5/2003 | Wu | 345/166 |
| 2004/0234107 A1* | 11/2004 | Machida et al. | 382/107 |
| 2004/0258274 A1* | 12/2004 | Brundage et al. | 382/100 |
| 2005/0019945 A1* | 1/2005 | Groll et al. | 436/169 |

* cited by examiner

APPARATUS AND METHOD FOR USING OPTICAL MOUSE ENGINE TO DETERMINE SPEED, DIRECTION, POSITION OF SCANNED DEVICE AND TO OBTAIN QUANTITATIVE OR QUALITATIVE DATA FROM SAME

FIELD OF THE INVENTION

The invention relates to an apparatus and method for reading lateral flow assay strips or other two-dimensional data collection devices with an optical mouse engine. More particularly, the invention relates to an apparatus and method for using the optical mouse engine to determine the speed, direction and position of a strip as it is inserted into and withdrawn from a reader, as well as to provide a quantitative and/or qualitative assessment of the optically visible information on the strip.

BACKGROUND OF THE INVENTION

Lateral flow tests and lateral flow assays are becoming increasingly useful for clinical diagnostics, veterinary diagnostics, environmental screening, drug screening and food tasting, among other applications. Exemplary lateral flow tests include, but are not limited to, a pregnancy test (i.e., hCG), fertility and ovulation tests (i.e., LH and FSH), infectious disease tests (e.g., HIV, Strep A, H. Pylori, HbsAg, and Mononucleosis), PSA, FP, human haemoglobin faecal and other cancer detection tests, cardiac markers, and drug tests (e.g., amphetamine, cocaine, BZO and THC).

In the past, lateral flow tests were primarily used for qualitative detection (i.e., yes or no as to existence of a selected condition). More recently, lateral flow assays have been developed for quantitative determination. For example, the quantitative determination of individual human proteins in biological fluids such as blood, plasma, serum, urine or cerebrospinal fluid provides an important tool for diagnosing diseases, as well as monitoring the course of diseases and particularly the effect of treatments therefor. Manual visual techniques for facilitating the reading of lateral flow assay results (e.g., selective placement of windows and use of color and indicia to improve viewing of visual test strip indicators) are being increasingly enhanced by automated optical detection systems. Optical instrument configuration and programming is important to achieving reliable and reproducible results. Optical detection systems can employ any of a number of methods such as the use of coated microspheres, superparamagnetic microspheres, remission or retransmission photometry, colorimetric techniques and fluorometric techniques.

An exemplary optical instrument or reader for a lateral flow strip is described in U.S. Pat. No. 6,394,952, to Anderson et al. The patent discloses an assay device in combination with a computer-assisted, reflectance-type reader having data processing software. The data processing software employs data reduction and curve fitting algorithms, optionally in combination with a trained neural network, for determining the presence or concentration of analyte in biological sample. This reader and other similar readers, however, can be relatively costly to implement and inaccurate. The process of inserting a test strip into a reader and removing it therefrom is subject to much variation that can skew test results. A need therefore exists for a reader that compensates for these variations. For example, a need exists for a reader that can detect test strip position therein and facilitate registration of the strip in the reader consistently for optimal reader results.

Optical navigation devices such as optical mouse engines have been developed to detect and track cursor movement in computer applications. In addition to cursor location, some optical mouse engines are provided with an additional function such as video imaging or image scanning. Exemplary optical mouse engines are described in U.S. Pat. No. 6,392,632, to Lee, in U.S. Pat. No. 6,281,882, to Gordon et al, and in U.S. Pat. No. 6,256,016, to Piot et al. None of these existing optical mouse engines, however, has been employed to read test strips for medical test data collection, nor to determine movement of a test strip within the reader to improve consistency of test strip position in the reader and therefore improve the accuracy of test strip results. A need therefore exists for a test strip reader employing optical engine technology that uses the built-in change of position detection in an optical engine to determine test strip position, movement and speed, and to facilitate improved quantitative and/or qualitative data collection using test strips.

SUMMARY OF THE INVENTION

An optical mouse engine-based reader is provided for accurate quantitative and/or qualitative reading and assessment of optically visual lines on rapid manual test strips, or other two-dimensional data collection devices.

In accordance with an aspect of the present invention, an optical engine (e.g., an imager/sensor operating in conjunction with a microcontroller or other processing device) is configured within a reader to determine a current position for a test strip that has been inserted into the reader. Internal self-test and diagnostic monitor algorithms are then performed to ensure that the strip is fully inserted and withdrawn with respect to the reader, and that all data from the reagent lines are within limits. The optical sensor has high speed data read rates and sensitivity to provide both accurate quantification of the reagent stripes on the strip and real-time motion information output as quadrature data. The microcontroller uses the motion information to determine the speed, direction and position of the strip as it is being inserted into and withdrawn from the reader by a user. Since the substantially exact position of the strip is known with respect to the reader, the microcontroller can calculate the optical absorption of each colored reagent line and, similarly, calculate the diagnostic significance (i.e., either qualitative or quantitative) of the scanned device.

In accordance with an embodiment of the present invention, a test strip reader comprises: (1) an optical sensor with an imaging array of pixels; (2) a light source; (3) a channel configured for receiving a test strip to be imaged by the test strip reader and for guiding the insertion and removal of the test strip with respect to the optical sensor, the test strip comprising optically detected information; (4) a lens positioned with respect to the imaging array and the light source to focus light from the light source that has been reflected from the test strip onto the imaging array, the optical sensor being operable to determine change of direction data corresponding to the position of the test strip with respect to the optical sensor; and (5) a processing device connected to the optical sensor for using the change of direction data to determine the position of the test strip with respect to the test strip reader, and for determining at least one of the optical absorptions of the information on the test strip, and diagnostic significance of the information on the test strip, with respect to the corresponding position of the test strip with respect to the test strip reader.

In accordance with another aspect of the present invention, the processing device is programmable to determine an average pixel value of at least part of a selected captured image by the imaging array and to store the average pixel value with data relating to the corresponding position of the test strip with respect to the test strip reader when the captured image was captured. The processing device is programmable to generate and store a plurality of average pixel values with data relating to the respective positions of the test strip with respect to the test strip reader, and to locate indicia on the test strip using the stored average pixel values and the data.

In accordance with a further aspect of the present invention, the processing device is programmable to determine if the test strip has been completely read by the optical sensor using data relating to the position of the test strip with respect to the test strip reader.

In accordance with yet another aspect of the present invention, the processing device is programmable to calculate the most likely target value of at least part of a selected captured image by the imaging array, and to store the most likely target value in a memory array mapped to the position of at least one of the indicia.

In accordance with still yet another aspect of the present invention, the optical sensor and the processing device are provided in an optical mouse engine.

In accordance with an aspect of the invention, a method of reading indicia from a test strip comprising the steps of: (1) moving a test strip relative to an imaging array of pixels, the test strip comprising optically detected information; (2) imaging at least part of the test strip using the imaging array of pixels; (3) generating change of direction data corresponding to the distance, rate and direction the test strip is moved relative to the imaging array; (4) using the change of direction data to determine the position of the test strip with respect to the test strip reader; and (5) determining at least one of the optical absorptions of the information on the test strip, and diagnostic significance of the information on the test strip, with respect to the corresponding position of the test strip with respect to the test strip reader.

In accordance with another aspect of the present invention, the method further comprises the steps of: (1) determining an average pixel value of at least part of a selected captured image by the imaging array; and (2) storing the average pixel value with data relating to the corresponding position of the test strip with respect to the test strip reader when the captured image was captured.

In accordance with another aspect of the present invention, the method further comprises the steps of: (1) generating and storing a plurality of average pixel values with data relating to the respective positions of the test strip with respect to the test strip reader; and (2) locating indicia on the test strip using the stored average pixel values and the data. The indicia can comprise at least one of a reference line, a test line, and a control line, and the method can further comprise the step of sensing thresholds for each of the reference line, the test line, and the control line to determine if the test strip has been completely read by the test strip reader.

In accordance with another aspect of the present invention, the method further comprises the steps of: (1) calculating the most likely target value of at least part of a selected captured image by the imaging array; and (2) storing the most likely target value in a memory array mapped to the position of at least one of the indicia. In addition, the method can further comprise the step of generating a most likely target value strip plot using a plurality of the stored values in the memory array.

In accordance with yet another aspect of the present invention, the method further comprises the step of determining if the test strip has been completely read by the optical sensor using data relating to the position of the test strip with respect to the test strip reader.

BRIEF DESCRIPTION OF THE DRAWINGS

These and other objects, advantages and novel features of the present invention will be readily appreciated from the following detailed description when read in conjunction with the accompanying drawings, in which.

Throughout the drawing figures, like reference numerals will be understood to refer to like parts and components.

DETAILED DESCRIPTION OF THE PREFERRED EMBODIMENTS

In accordance with the present invention, a reader having an optical mouse engine is provided for reading a test strip such as a Directigen lateral flow assay strip or other similar rapid manual test. The reader can also be used to collect data for other medical test data collection applications employing, for example, two-dimensional electrophoresis gels or multiple analyte, multi-stripe, lateral flow assays, among other data collection devices. As used herein, a test strip refers to any media on which patient test data or other data is generated, recorded, or displayed in a manner that forms an image or from which an image can be generated via the optical mouse engine. Such strips can include, but are not limited to, immunochromatographic test strips (e.g., lateral flow devices), x-ray films, radiographic assay films or images, films produced from sequencing gels, EKG printouts, MRI results, among others. Although referred to as a strip, media that can be read using an optical mouse engine in accordance with the present invention can be of essentially any shape or geometry and size.

As stated above, the process of inserting a test strip into a reader and removing it therefrom is subject to much variation that can skew test results. The instrument reader of the present invention compensates for these variations by tracking the speed and direction of movement of the test strip with the optical mouse engine and eliminating variations using a synchronization algorithm such as the algorithm described below in connection with FIG. 8. In addition, the reader is programmable to obtain quantitative and/or qualitative information from the device (e.g., test strip) that is being read.

Figure 1:
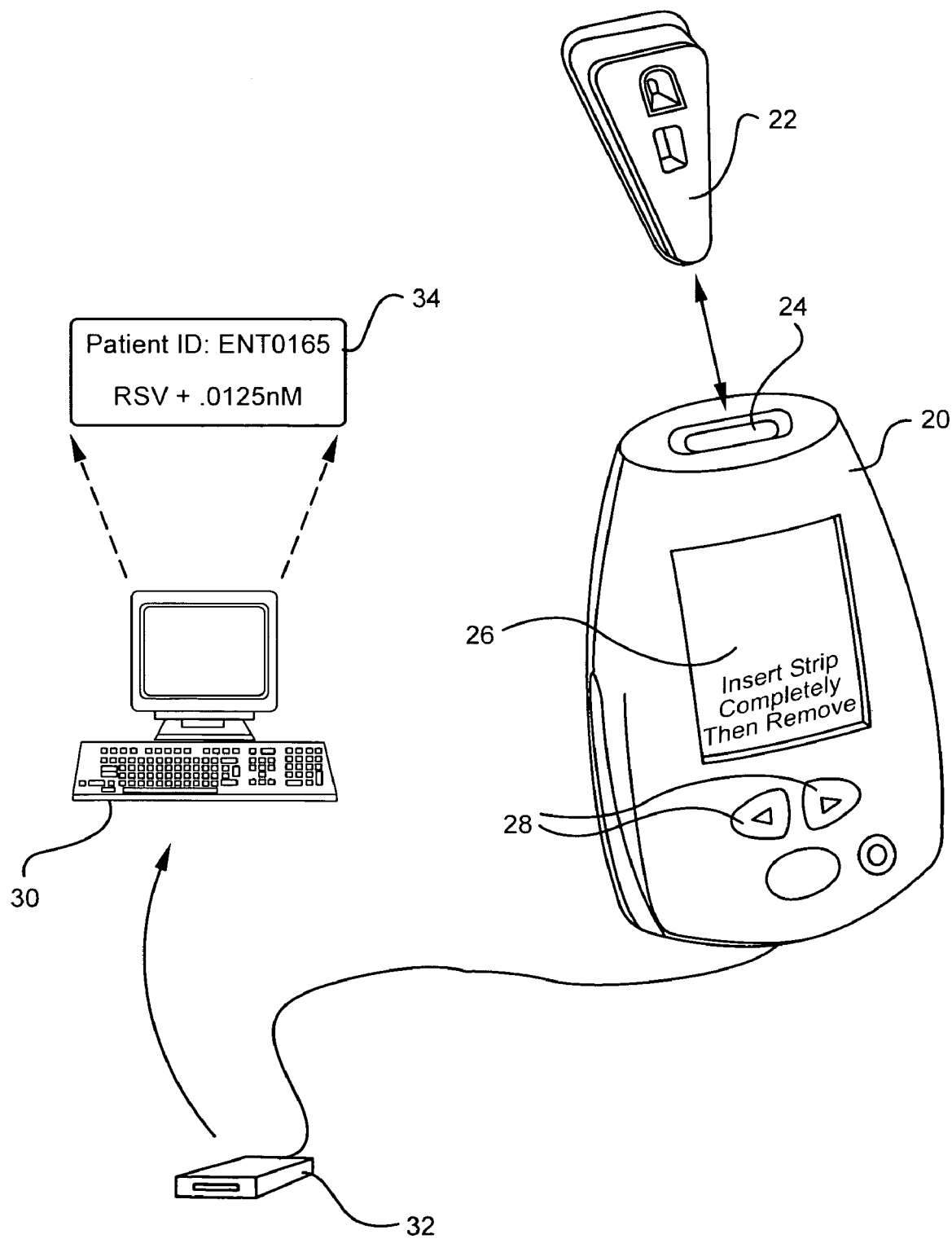
FIG. 1 is a diagram of a test strip reader connected to a computer via a USB connection in accordance with an embodiment of the present invention.

With reference to FIG. 1, an exemplary reader 20 is depicted in accordance with an embodiment of the present invention. The reader 20 is preferably implemented as a handheld device that is portable and battery-operated. The reader comprises an opening 24 into which a test strip 22 or other device to be read is inserted. In the illustrated example, the test strip is a rapid manual flow strip. It is to be understood that the reader 20 can be configured differently to accommodate other types of data collection devices such as a two-dimensional electrophoresis gel.

With continued reference to FIG. 1, the reader 20 preferably comprises a display 26 and optional control buttons indicated generally at 28. The display can provide test results, instructions, error messages, and the like. Data from the reader 20 can be provided to a computer 30 (e.g., a personal computer (PC)) via a USB connector 32, or be reader-resident for simpler applications. The USB and USB controller of the PC 30 can supply power, as well as a USB connection to the reader 20. The PC 30 is provided with application software indicated generally at 34 for test logging and report generation, among other functions.

Figure 2:
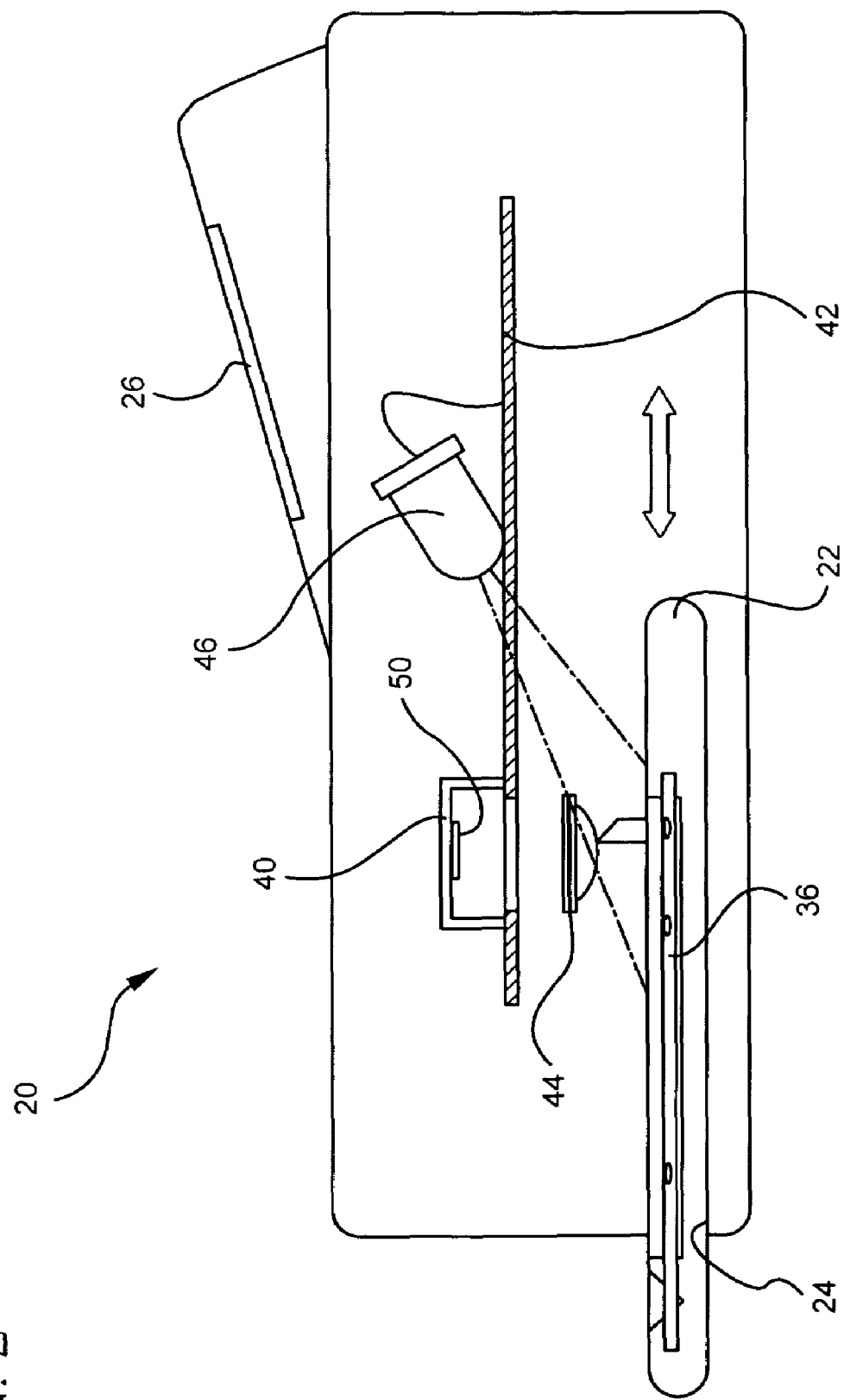
FIG. 2 is a side view of a test strip reader constructed in accordance with an embodiment of the present invention.

The reader 20 will now be described in more detail in connection with FIGS. 2 and 3. The reader 20 is advantageous in that it is relatively low cost and has no moving parts, except for the insertion and withdrawal of the test strip 22 by a user. The reader 20 is shown with a rapid manual test cartridge 22 inserted at least partially into the reader opening 24. The cartridge comprises a lateral flow test substrate 36 showing reagent development. The reader 20 preferably employs an optical mouse engine 80 (FIG. 6) which comprises the Agilent ADNS-2051 optical mouse sensor 40 available from Agilent Technologies, Inc. connected to a microcontroller 70 described in more detail below. The Agilent ADNS-2051 sensor 40 is configured as a 16-pin staggered dual inline package (DIP) that is designed for mounting on a through-hole printed circuit board (PCB) 42. An illuminating device such as a light emitting diode (LED) 46 is provided to illuminate the surface 36 of the device 22 being read by the optical mouse sensor 40. A lens 44 or light pipe focuses the light from the LED 46 onto an array 50 (e.g., CMOS array) of the optical mouse sensor 40 through an aperture 48 of the PCB 42.

Figure 3:
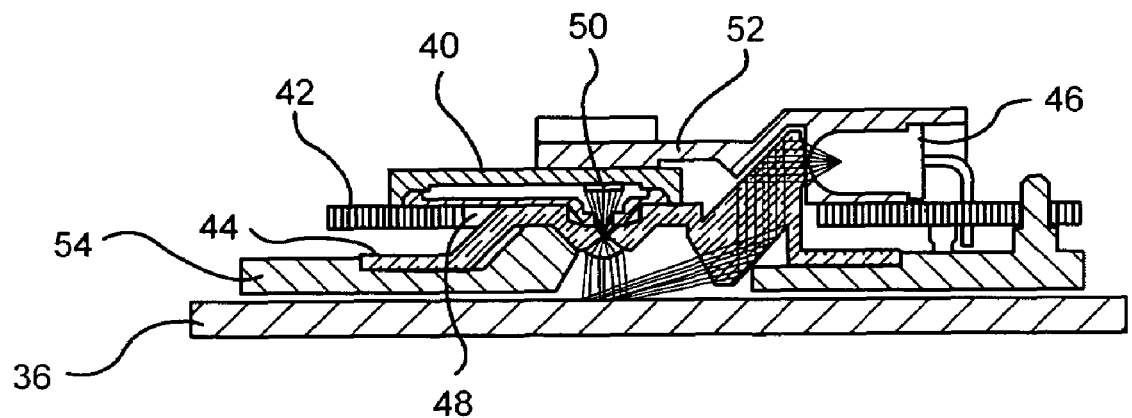
FIG. 3 is a side view of a printed circuit board assembly for a test strip reader constructed in accordance with an embodiment of the present invention.
Figure 4:
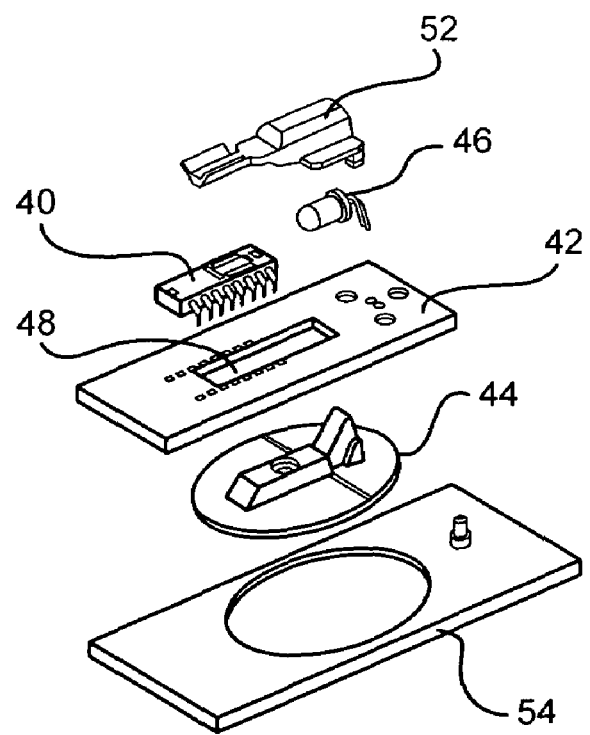
FIG. 4 is an exploded, isometric view of many of the components of the printed circuit board assembly for a test strip reader depicted in FIG. 3.
Figure 5:
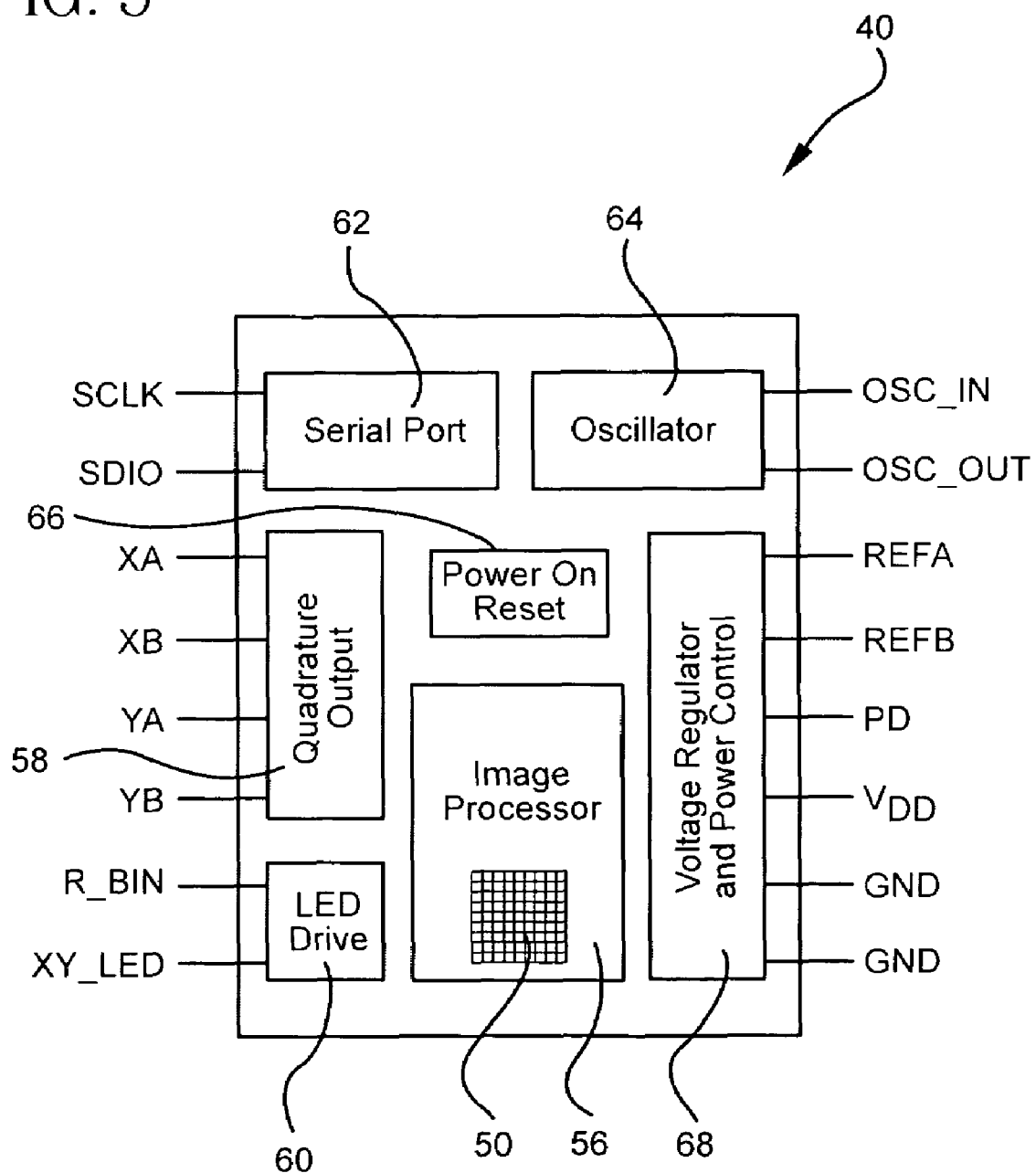
FIG. 5 is a block diagram of an optical mouse sensor employed in accordance with an embodiment of the present invention.

FIGS. 3 and 4 illustrate an exemplary and more detailed PCB assembly for the reader 20. A clip 52 is used to mount the LED 46 on the PCB 42. The lens 44 is mounted onto a base plate 54. The optical position reference for the PCB 42 is set via the base plate 54 and the lens 44. A block diagram of the sensor 40 is provided in FIG. 5, including an image processor 56 for the array 50, a quadrature output 58, an LED drive 60, a serial port 62, an oscillator 64, a power on reset 66 and a voltage regulator and power control module 68.

The LED 46 is preferably customized for the target properties (i.e., the properties of the strip or other device being read). For a lateral flow assay employing colloidal gold particles, an LED 46 is selected with an absorption or excitation wavelength that varies depending on the size of the colloidal gold particles. If a fluorescent assay is used, then an LED 46 is selected with the excitation wavelength of that fluorescent material. Similarly, with other colorimetric targets, the color and/or wavelength of the LED 46 is optimized for that target to give the best response.

The lens 44 can also be customized. The optical integrated circuit 40 is equipped with an aspherical lens that maps the two-dimensional image it is reading onto its array 50 in a 1:1 configuration. It can be desirable (e.g., when reading stripes on the surface 36 of a lateral flow assay strip 22) to concentrate the strips into a particular zone of the array. Accordingly, a combination of an aspherical lens with a cylindrical lens can be used to achieve such a concentration.

Figure 6:
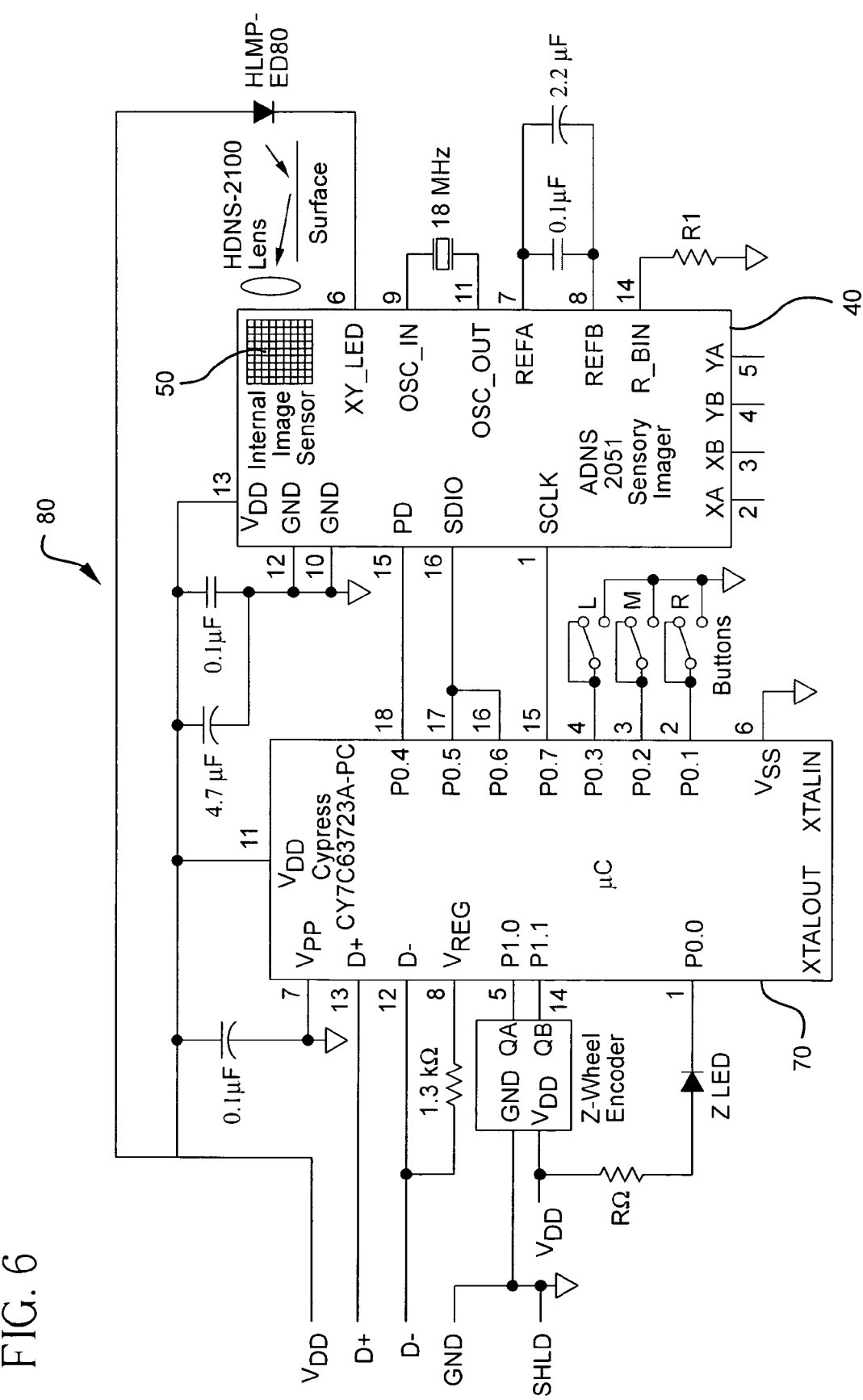
FIG. 6 is a schematic diagram of an optical mouse engine comprising an optical mouse sensor and a microcontroller employed in accordance with an embodiment of the present invention.

As stated above, the reader 20 preferably employs an optical mouse engine 80 that is mounted on the PCB 42 such that the sensor 40 can receive light from the surface being read through a lens 44. With reference to FIG. 6, the optical mouse engine 80 preferably comprises a microcontroller 70 configured to receive the outputs of the optical mouse sensor 40. The outputs can be via the quadrature output pins or the SDIO pin in the sensor 40. The microcontroller 70 is preferably a CYPRESS CY7C63723A-PC available from Cypress Semiconductor Corporation. The software for the reader 20, including the algorithms for determining strip 22 position with respect to the reader and for providing a quantitative and/or qualitative assessment of the optically visible data on the strip 22 based on the output of the sensor 40, is preferably generated in code (e.g., C program language), compiled and downloaded to the microcontroller 70 via the USB controller in the PC 30 and the USB connector 32.

The overall operation of the reader 20 will now be discussed, followed by an illustrative hardware implementation, and finally a description of the algorithms implemented in accordance with the present invention to determine the position of the test strip 22 in the reader and to obtain quantitative and/or qualitative information from the test strip 22. Upon insertion of a test strip 22 into the reader 20 by a user, the power level of the optical mouse engine is changed from a low power mode to a higher power mode, the LED 46 or other light source is illuminated, and all of the digital devices enter a reset routine.

The user slides the test strip 22 all the way into the hand-held reader 20, or underneath depending on the reader configuration, while the optical mouse engine 80 records the reagent line intensity or absorbance and each stripe's position on the nitrocellulose substrate of the test strip 22. All of this optical read data is then output from the sensor 40 to the on-board microcontroller 70. Internal self-test and diagnostic monitor algorithms are then performed to ensure that the strip is fully inserted and withdrawn with respect to the reader, and that all data from the reagent lines are within limits. If not, an error message is displayed on the LCD 26 of the reader 20. The microcontroller 70 then calculates the test line reading, reference line reading and control line reading (e.g., whether it be calorimetric, fluorescent, luminescent or otherwise optically differentiable) and outputs the calculated rapid test results to the LCD 26.

Thus, to summarize, the optical sensor 40 has high speed data read rates and sensitivity to provide both accurate quantification of the reagent stripes on the strip and real-time motion information output as quadrature data, for example. The microcontroller 70 incorporated into the hand-held reader 20 can use this output information to determine with precision the speed, direction and position of the strip 22 as it is being inserted into and withdrawn from the reader 20 by a user. Since the substantially exact position of the strip 22 is known with respect to the reader 20, the microcontroller 70 can calculate the optical absorption of each colored reagent line and, similarly, calculate the diagnostic significance (i.e., either qualitative or quantitative) of the scanned device.

Illustrative Implementation of Reader 20 using an Agilent Optical Mouse Engine 80

Hardware: In accordance with one embodiment of the present invention, the Agilent ADNS-2051 chip is used as the optical motion sensing device 40. The Cypress Semiconductor Corporation CY7CG3723 enCore chip is used for the microcontroller 70 and contains the hardware necessary to communicate with the Agilent ANDS-2051 chip, as well as the hardware necessary to communicate with a PC 30 over a USB connection. Both of these chips can be found together in commercially available optical mouse devices. One such mouse was acquired from Cypress Semiconductor Corporation and used as a development platform for the exemplary implementation described below. An advantage this Cypress mouse 80 has over other optical mice is that the Cypress microcontroller 70 is socketed in the Cypress mouse, making it easier to use with a Cypress in-circuit emulator. The CY3654 in-circuit emulator was used in developing firmware for the microcontroller 70.

Mouse Firmware: Firmware for the optical mouse 80 comprising the sensor 40 and the microcontroller 70 is preferably implemented to achieve a combined USB and PS/2 mouse. For example, a demonstration package can be downloaded from the Internet that includes firmware for a mouse 80 utilizing the Agilent and Cypress chips 40 and 70, respectively, described above. The USB interface in the mouse firmware is configured using the USB and HID specifications to achieve an efficient USB interface. The Agilent chip 40 makes available data that is not normally used by the host PC 30 when communicating with an optical mouse 80. The Agilent ADNS-2051 Optical Mouse Sensor Data Sheet gives a complete description of the data and is incorporated by reference herein. The Agilent chip 40 makes available an image of 16×16 pixels, each with a range of 0 to 63 counts. The microcontroller 70 collects pixel data from the Agilent chip 40 one pixel at a time. The USB interface via connector 32 is limited to sending 8 bytes of data from the microcontroller 70 to the PC 30 each time the PC 30 polls the device 20. The mouse 80 is preferably programmed to collect 8 pixels from the Agilent chip 40 and send them back to the PC 30, along with a group number indicating where in the image the 8 pixels came from. Thus, the minimum time to transfer a complete image from the mouse 80 to the PC 30 is (32 pixel groups)×(10 ms) or 0.32 seconds. This agrees with the rate the PC 30 displays images on its screen.

PC 30 Application Software: A generic USB application can be downloaded from the Internet for a starting point to create an application that interfaces to the target mouse 80. The firmware in the mouse is configured to appear as a user defined HID USB device. The PC 30 operating system detects the device automatically and loads a generic HID USB driver. Applications on the PC 30 communicate with the mouse 80 through the USB driver using standard API calls. During an illustrative startup sequence, the PC application interrogates the USB driver to find the device it wants to communicate with. The application asks for a list of all HID devices connected to the system. It then interrogates each device individually, asking the device for its vendor code and product code. When the application finds the device it is looking for, it opens the device for reading and writing.

With regard to USB communications, USB devices such as the reader 20 are generally slaves in the communication process with the host PC 30. When a USB device has data to send to the host, it buffers the data and waits for the host PC 30 to poll it. During the enumeration process, the USB device indicates how often the host should poll the device for data. In the case of the reader 20, the polling is preferably set up for the fastest rate available to a low speed USB device, that is, 10 ms.

Several aspects of the sensor 40 and, particularly, the Agilent integrated circuit, will now be described.

Pixel Dump: The pixel dump operation does not take a snapshot of the pixel image and make it available to the microcontroller 70 as might be expected. The sensor 40 instead passes pixels to the microcontroller 70 from the image that happens to be in the image buffer when the pixel is transferred. This aspect of the sensor 40 is verified by positioning the mouse 80 such that the image displays a horizontal line through the image. The mouse is then moved up and down as the images are displayed on the PC 30 screen. The horizontal line is displayed as a wavy line on the screen indicating that each image is made from pixels taken from several images over time.

Auto Gain Control Circuitry: The sensor 40 (e.g., the Agilent chip) comprises an auto gain control (AGC) circuit that attempts to maintain a level of contrast in the image. The AGC circuit does this by changing the integration time of the imager as the brightness of the image changes. The aforementioned data sheet for the Agilent ADNA-2051 optical mouse sensor states that the AGC circuit adjusts the integration time to keep the brightest pixel in the mid-50s. In use, however, it appears that the AGC circuit attempts to keep the average value of all pixels within some range. Two observations support this. When the imager is over a black-white interface with only a corner of the image over white, the white pixels are reported at full scale. Also, the smoothness of the pixel average per integration time data suggests the average pixel value is being controlled.

Motion Sensing: The motion sensing ability of the Agilent ADNS-2051 optical mouse sensor remains intact while images are read from the chip. This can be useful to determine the position of a strip 22 in a reader 20.

An adjustment to the hardware configuration of the mouse 80 may be needed if a problem is encountered when reading the surface of a lateral flow strip 22. The surface of the lateral flow strip may not have the properties necessary for a particular sensor 40 (e.g., the Agilent chip) to determine motion. For example, the Agilent chip must see a minimum number of what are referred to as "features" in order to determine motion. These features appear to be a combination of color pattern and texture in the surface that the mouse 80 is on. It appears that the number of features must be above 16 for the Agilent chip to report motion. While reading lateral flow strips, the number of features seen by the Agilent chip is often as low as 4. Accordingly, the microcontroller 70 can be interfaced to two sensors 40 (e.g., two Agilent chips) such that one of the two Agilent chips is directed at a textured surface or an index marked surface (e.g., a gray code, bar code, and so on) and supplies motion and position information to the microcontroller 70, while the other Agilent chip is directed at the target stnp.

LED Illumination: The LED or light source 46 that illuminates the target surface 36 travels through a folded tunnel and a lens 44 in the illustrative embodiment of FIG. 3. The light hits the target surface at a relatively high angle. This not only allows the light source 46 to be mounted well away from the imager in the sensor 40, but also enhances the contrast seen by the imager by using the surface texture to cast shadows. The mouse application 80 is preferably configured to see a lot of features in the surface to work most effectively.

The LED 46 light is not uniform on the target surface 36. It is easy to see a pattern where the imager in the sensor 40 is reading the surface. The low angle that the light hits the target surface 36 makes the position of the target surface 36 to the base of the mouse 80 an important consideration. A slight difference in the target distance from the imager causes a different part of the LED light pattern to be visible to the imager. This is evident when trying to measure a surface by hand. With the mouse 80 held stationary, applying and releasing vertical pressure on the mouse 80 causes the average pixel per shutter value to change.

Since a surface that a mouse will be used on will usually be very flat, the conventional mouse application (i.e., cursor movement on a PC display) is probably not very sensitive to this problem. However, data collected from test strips 22 using an optical mouse 80 in accordance with the present invention can be affected because the flatness of the strips 22 as they are mounted to the stage (e.g., inserted into a reader 20) cannot be determined to any significant degree. Thus, the light source 46 is configured to be as uniform as possible in any implementation of the present invention using the Agilent chip or similar imager.

Data collection considerations for the reader 20 of the present invention, and particularly a reader employing the Agilent chip mentioned above for the sensor 40, will now be discussed.

Calibration Values for various LEDs 46 that can be used in the mouse 80: Calibration is performed by locating the imager in the sensor 40 over the darkest area to be tested on a target surface 36, and recording the shutter and average pixel values reported by the imager. With regard to the present invention, the darkest area is generally the control line of the test strip. The imager is then moved over the brightest area to be tested, which is typically the plain white area of the test strip 22, and the average pixel value reported by the imager is recorded.

In accordance with an aspect of the present invention, the average pixel value is calculated from the 256 pixels reported by the imager 40 rather than the pixel average reported by the imager 40. This provides more resolution since the average pixel reported by the imager is only a 6-bit value.

The data from the imager 40 is used to calculate a current brightness, between the values obtained for the dark control line and white background, by calculating the average of the current pixels in the image, and combining that average with the current shutter value reported by the imager as follows:

$$pixel = \frac{(pixel\_ave/shutter) - (low\_pixel\_ave/low\_shutter)}{(high\_pixel\_ave/high\_shutter)} * max\_pixel$$

This calculation gives a value in a pixel value in a specific range. The pixel_ave, max_pixel are from the Agilent chip registers. The low_shutter and high_shutter values are from historical shutter_values. The low_pixel_ave and high_pixel_ave are from historical_pixel_ave values. The plots obtained from the test strips plotted a value calculated as follows:

value=(pixel_ave/shutter)*1000

For original red LED calibration values, the average shutter value is normalized for low scale by taking a reading over the control line of a test strip. The high scale is measured over the background part of the test strip. The values (hexadecimal) are as follows:
Control line—shutter: 180 h, average: 30 h
Background—shutter: 123 h, average: 2 Dh Similarly, for blue-green LED calibration values, the values are as follows:
Control line—shutter: BD7 h, average: 25 h
Background—shutter: 7DAh, average 29 h Data Collection for Plots: To collect data for the exemplary plots depicted in FIG. 7, the optical mouse 80 was mounted horizontally on a light bench. The test strip 22 to be scanned was mounted to an x-y-z stage such that the strip was located horizontally against the bottom of the mouse. The relative positions of the mouse and stage were such that the horizontal motion of the stage could move the strip along the bottom of the mouse. The movement of the stage was long enough to image from past the control line on the strip to past the test line on the strip.

The PC application 34 opened a data file upon startup and provided a button to the user that, when pressed, wrote the pixel average/shutter value from the most recent image scan to the data file. The horizontal stage was moved to one extreme past the control line. A data point was collected and the knob on the horizontal stage was then turned one-half rotation. This continued until the stage reached its other limit. The PC application 34 was discontinued, and the collected data was provided to a spreadsheet. After six test strips 22 were scanned, the graph in FIG. 7 was generated.

Microcontroller 70 Operation

Figure 8:
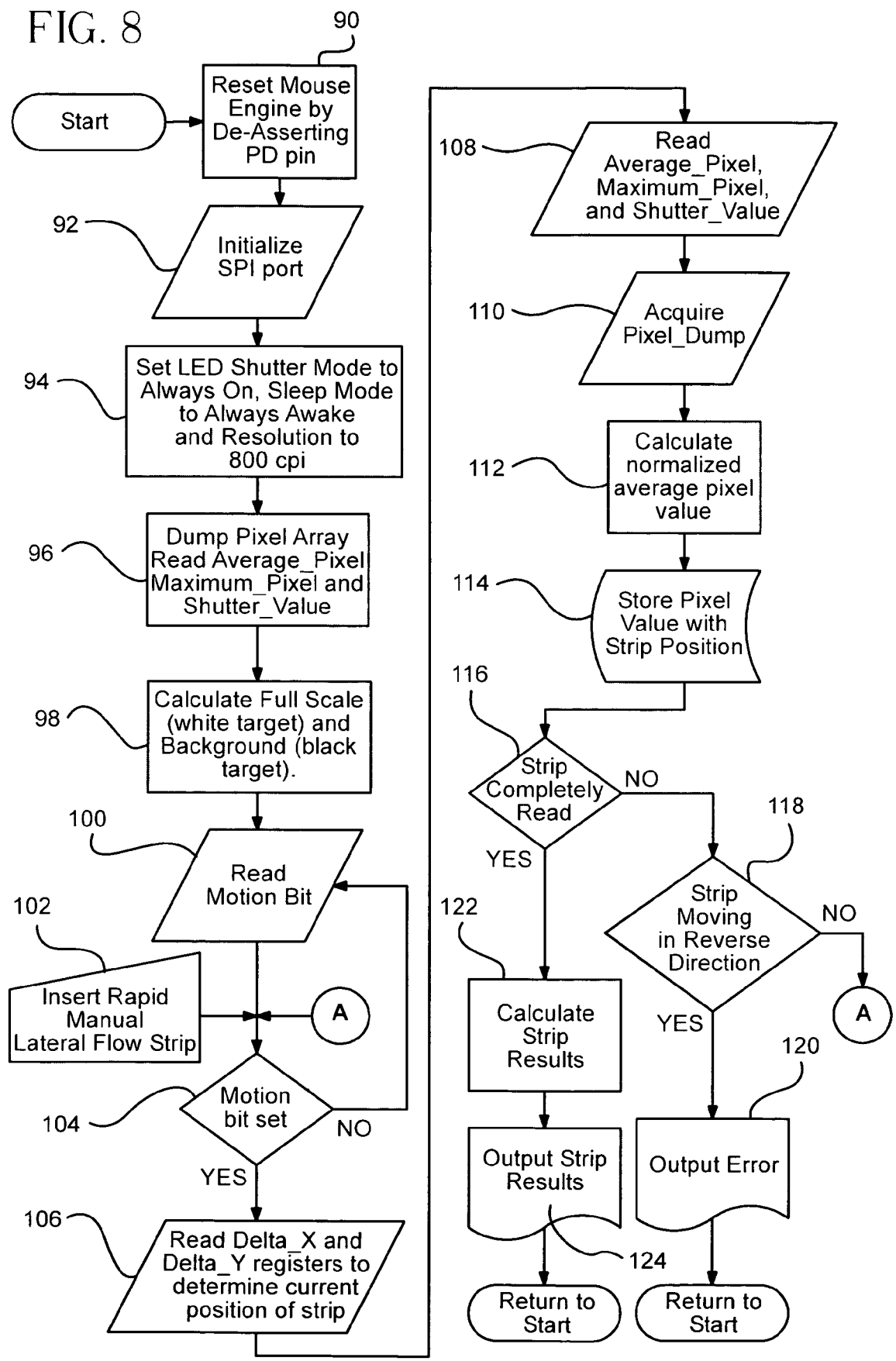
FIG. 8 is a flow chart depicting a sequence of operations for initializing hardware/firmware in a test strip reader in accordance with an embodiment of the present invention.
Figure 9:
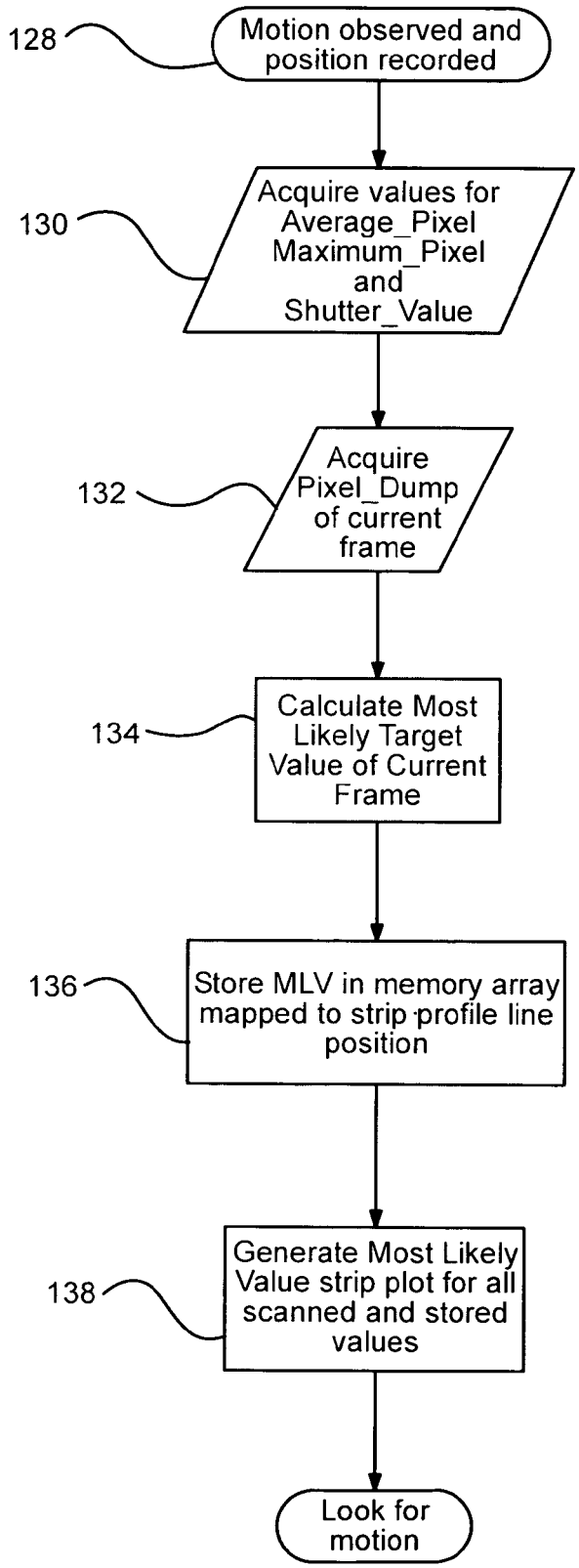
FIG. 9 is a flow chart depicting a sequence of operations for data collection using the test strip reader in accordance with an embodiment of the present invention.

The programmable operations of the microcontroller 70 with respect to the optical sensor 40 and the PC 30 will now be discussed in further detail in connection with the flow charts in FIGS. 8 and 9. FIG. 8 describes an overall procedure for initializing hardware/firmware in the reader 20 in accordance with the present invention. FIG. 9 describes data collection more specifically in accordance with the present invention. Although the programmed operations described below are described with reference to the Agilent chip for the sensor 40, the programmed operations are not limited to such an implementation. The operations can be used with other types of microcontrollers and optical mouse sensors.

With reference to FIG. 8, the mouse sensor 40 is reset (block 90). When the Agilent chip is used, reset occurs by de-asserting the PD pin. In addition, the serial port of the sensor 40 is initialized (block 92). In the exemplary implementation where the Agilent chip is used, the SPI port is initialized. The LED shutter is set to be on and its resolution is selected (block 94). The LED settings for the Agilent chip are preferably 800 counts per inch (cpi) resolution, shutter mode is always on, and sleep mode is always awake. As stated above, calibration is performed by locating the sensor 40 over the darkest area to be tested (e.g., the control line of the test strip) and recording shutter and average pixel values reported by the sensor 40. The imager 40 is then moved over the brightest area to be tested (e.g., the plain white area of a test strip 22) and the average pixel value reported by the imager 40 is also recorded by the microcontroller 70. As indicated in block 96, these values are then obtained from the sensor 40, as well as the values of the current pixel array or frame for the surface being imaged. The Agilent chip, in particular, employs a pixel dump command and maintains registers for storing such values as Average_Pixel, Maximum_Pixel and Shutter_Value. Using these values, the full scale or white target is calculated, as well as the background or black target (block 98).

The microcontroller 70 then proceeds to determine if the surface beneath the lens, such as a strip 22, has moved and collects X and Y direction data. As stated above, the output format of the Agilent chip is two channel quadrature (i.e., X and Y direction) which emulates optical encoder phototransistors. The current X and Y information is available in registers of the sensor 40 and accessed via a serial port. The default resolution is 400 cpi with motion rates up to as many as 14 inches per second. The resolution, however, can also be programmed to 800 cpi. The Agilent chip maintains a number of registers such as a motion register and Delta_X and Delta_Y registers which are read sequentially. In other words, the motion register can be read to allow a user to determine if motion has occurred since the last time the motion register was read. The Delta_X and Delta_Y registers are then read to determine the accumulated motion. The counts in these registers correspond the number of pixel state changes up to the maximum cpi (e.g., 400 or 800) since the last position register dump.

With continued reference to FIG. 8, a motion register bit is set (e.g., high or low depending on whether or not motion is detected) by the sensor 40. The motion bit is read from the sensor 40 (block 100). If the motion bit is not set to indicate that motion was detected with respect to the surface being imaged, then the microcontroller 70 continues to read the motion bit setting, as indicated by the negative branch of decision block 104. If, for example, a rapid manual lateral flow strip has been inserted with respect to the reader 20 (block 102), then the microcontroller 70 reads a motion bit that has been set by the sensor 40 to indicate motion. As indicated by the affirmative branch of the decision block 104 and block 106, the microcontroller 70 then proceeds to read Delta_X and Delta_Y registers from the Agilent chip, or similar information if another type of sensor 40 is used, to determine the current position of the strip 22.

With reference to blocks 108 and 110 of FIG. 8, the values of Average_Pixel, Maximum_Pixel and Shutter_Value are read and a pixel dump is acquired for the current location of the target (e.g., strip) which has been determined to be in motion. The normalized, average pixel value is then calculated (block 112). As stated previously, the average pixel value is calculated from the 16×16 or 256 pixels reported by the imager 40 rather than the pixel average value reported by the imager 40. This provides more resolution since the average pixel reported by the imager is only a 6-bit value. The calculated pixel value is then stored along with the strip 22 position (i.e., the position on the target strip with respect to the current frame position as determined from the motion registers by the microcontroller 70).

As indicated by the decision block 116 in FIG. 8, the microcontroller 70 is programmed to determine if the strip 22 has been completely read by sensing the threshold of all three lines (i.e., reference, test and control lines) or by timeout. With reference to blocks 122 and 124, the microcontroller 70 can be programmed to calculate strip results (e.g., the test line reading, reference line reading and control line reading) based on the stored calculated pixel values and their corresponding strip position such as the number of lines detected on the strip, their relative spacing, their relative brightnesses, and so on. These results can then be output via the display 26 or the PC 30 monitor. An example is discussed in FIG. 9 below.

If the strip 22 has not been completely read, and is moving in the reverse direction, an error message (block 120) is generated on the screen 26, for example; otherwise, the microcontroller proceeds to look for motion of the strip 22 (negative branch of decision block 118).

Figure 7:
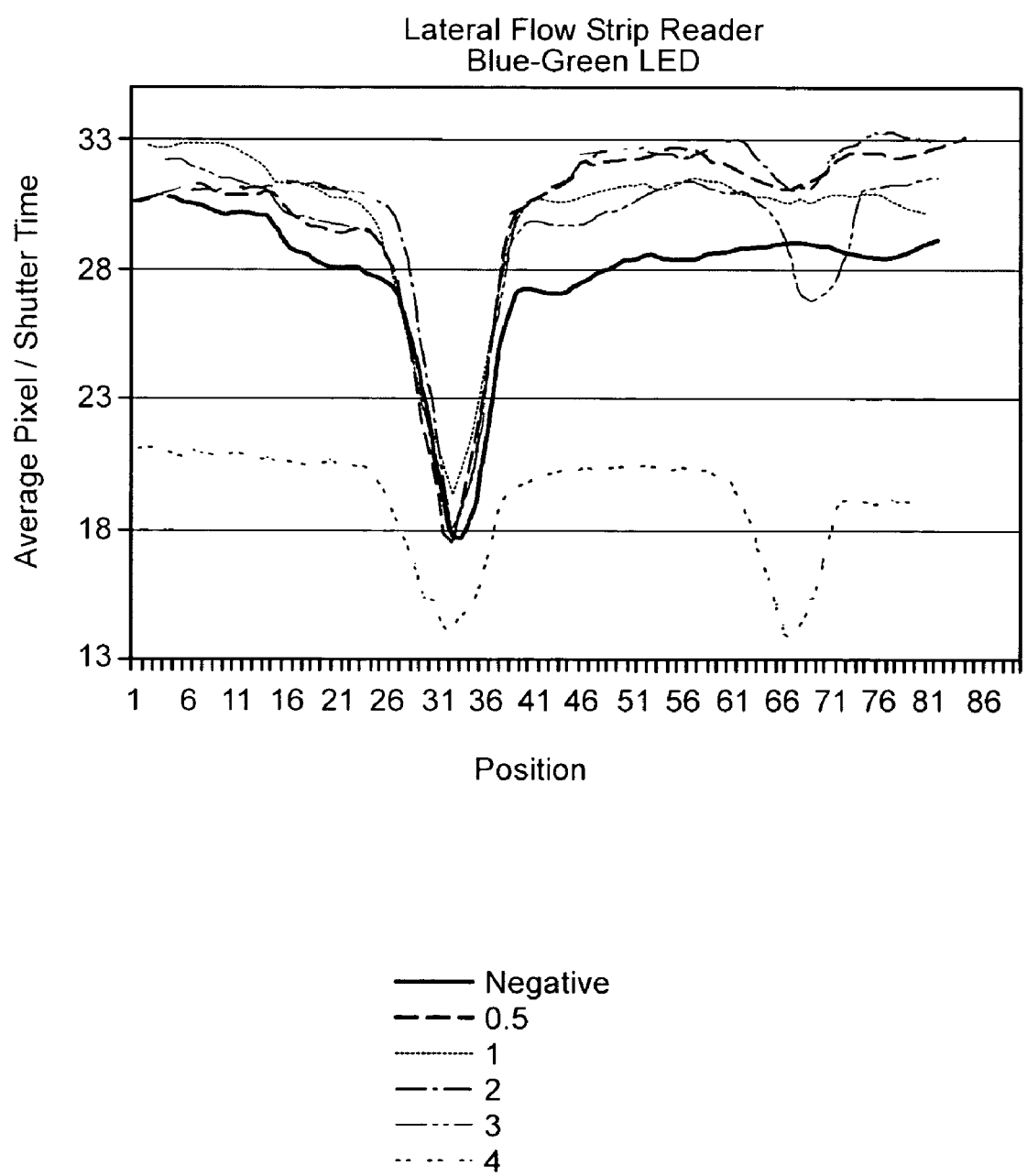
FIG. 7 is a test strip plot generated in accordance with an embodiment of the present invention.

A data collection operation in accordance with one embodiment of the present invention will now be described with respect to FIG. 9. As indicated in block 128, motion is observed and strip 22 position is recorded by the microcontroller in a manner such as that described in FIG. 8. The values of Average_Pixel, Maximum_Pixel and Shutter_Value are acquired (block 130), as well as a pixel dump (block 132) for the current frame of the strip 22. The microcontroller is programmed to calculate the Most Likely Target Value (MLV) of the current frame (block 134). The MLV is stored in a memory array that is mapped to the strip profile line position (block 136). An MLV strip plot is then generated for all scanned and stored values (block 138), as shown in FIG. 7. The microcontroller 70 then proceeds to look for more motion and can repeat the process shown in FIG. 9.

In accordance with other aspects of the present invention, the reader can be configured to perform barcode reading (e.g., for test identification), and can be provided with built-in memory for storage of test results and a connection device(s) for interconnectivity with a BD.id terminal or Laboratory Information System.

Although a lateral flow assay strip such as the Directigen is discussed herein as an illustrative embodiment, it is to be understood that the optical mouse-based reader of the present invention is not limited to colorimetry but can also be used for fluorescence, grayscale, luminance, bioluminance and other optical interrogation techniques that can be assayed by an image array.

Although the present invention has been described with reference to a preferred embodiment thereof, it will be understood that the invention is not limited to the details thereof. Various modifications and substitutions will occur to those of ordinary skill in the art. All such substitutions are intended to be embraced within the scope of the invention as defined in the appended claims.

What is claimed is:

1. A test strip reader comprising:
   an optical sensor with an imaging array of pixels;
   a light source;
   a channel configured for receiving a test strip to be imaged by the test strip reader and for guiding the insertion and removal of the test strip with respect to the optical sensor, the test strip comprising optically detected information;
   a lens positioned with respect to the imaging array and the light source to focus light from the light source that has been reflected from the test strip onto the imaging array, the optical sensor being operable to determine change of direction data corresponding to the position of the test strip with respect to the optical sensor; and
   a processing device connected to the optical sensor for using the change of direction data to determine the position of the test strip with respect to the test strip reader, and for determining at least one of the optical absorptions of the information on the test strip, and diagnostic significance of the information on the test strip.

2. A test strip reader as claimed in claim 1, wherein the processing device is programmable to determine an average pixel value of at least part of a selected captured image by the imaging array and to store the average pixel value with data relating to the corresponding position of the test strip with respect to the test strip reader when the captured image was captured.

3. A test strip reader as claimed in claim 2, wherein the processing device is programmable to generate and store a plurality of average pixel values with data relating to the respective positions of the test strip with respect to the test strip reader, and to locate indicia on the test strip using the stored average pixel values and the data.

4. A test strip reader as claimed in claim 3, wherein the processing device is programmable to calculate the most likely target value of at least part of a selected captured image by the imaging array, and to store the most likely target value in a memory array mapped to the position of at least one of the indicia.

5. A test strip reader as claimed in claim 1, wherein the optical sensor and the processing device are provided in an optical mouse engine.

6. A test strip reader as claimed in claim 1, wherein the processing device is programmable to determine if the test strip has been completely read by the optical sensor using data relating to the position of the test strip with respect to the test strip reader.

7. A method of reading indicia from a test strip comprising the steps of:
- moving a test strip relative to an imaging array of pixels, the test strip comprising optically detected information;
- imaging at least part of the test strip using the imaging array of pixels;
- generating change of direction data corresponding to the distance, rate and direction the test strip is moved relative to the imaging array;
- using the change of direction data to determine the position of the test strip with respect to the test strip reader; and
- determining at least one of the optical absorptions of the information on the test strip, and diagnostic significance of the information on the test strip.

8. A method as recited in claim 7, further comprising the steps of:
- determining an average pixel value of at least part of a selected captured image by the imaging array; and
- storing the average pixel value with data relating to the corresponding position of the test strip with respect to the test strip reader when the captured image was captured.

9. A method as recited in claim 8, further comprising the steps of:
- generating and storing a plurality of average pixel values with data relating to the respective positions of the test strip with respect to the test strip reader; and
- locating indicia on the test strip using the stored average pixel values and the data.

10. A method as recited in claim 9, wherein the indicia comprises at least one of a reference line, a test line, and a control line, and further comprising the step of sensing thresholds for each of the reference line, the test line, and the control line to determine if the test strip has been completely read by the test strip reader.

11. A method as recited in claim 9, further comprising the steps of:
- calculating the most likely target value of at least part of a selected captured image by the imaging array; and
- storing the most likely target value in a memory array mapped to the position of at least one of the indicia.

12. A method as recited in claim 11, further comprising the step of generating a most likely target value strip plot using a plurality of the stored values in the memory array.

13. A method as recited in claim 7, further comprising the step of determining if the test strip has been completely read by the optical sensor using data relating to the position of the test strip with respect to the test strip reader.

* * * * *